United States Patent [19]

Monin et al.

[11] Patent Number: 4,606,636
[45] Date of Patent: Aug. 19, 1986

[54] OPTICAL APPARATUS FOR IDENTIFYING THE INDIVIDUAL MULTIPARAMETRIC PROPERTIES OF PARTICLES OR BODIES IN A CONTINUOUS FLOW

[75] Inventors: Jean Monin; Bernard Faure; Georges Soldat; Jean-Claude Healy, all of Saint-Etienne, France

[73] Assignee: Universite de Saint-Etienne, France

[21] Appl. No.: 545,100

[22] Filed: Oct. 25, 1983

[51] Int. Cl.$^4$ ............................................. G01N 21/49
[52] U.S. Cl. ..................................... 356/338; 356/318
[58] Field of Search ............... 356/336, 338, 339, 410, 356/318; 250/574, 576

[56] References Cited

U.S. PATENT DOCUMENTS

| | | | |
|---|---|---|---|
| 3,457,407 | 7/1969 | Goldberg | 356/338 |
| 3,508,830 | 4/1970 | Hopkins et al. | 356/338 |
| 3,932,762 | 1/1976 | Moser | 250/574 |
| 3,985,441 | 10/1976 | Schoeffel et al. | 356/246 |
| 4,124,302 | 11/1978 | Kuzmin | 356/440 |
| 4,189,236 | 2/1980 | Hogg et al. | 356/336 |
| 4,200,802 | 4/1980 | Salzman et al. | |
| 4,273,443 | 6/1981 | Hogg | 356/343 |
| 4,311,387 | 1/1982 | deMey et al. | 356/410 |
| 4,348,107 | 9/1982 | Leif . | |
| 4,422,761 | 12/1983 | Frommer | 356/338 |
| 4,479,058 | 10/1984 | Gast et al. | 250/343 |

FOREIGN PATENT DOCUMENTS

| | | |
|---|---|---|
| 1931631 | 1/1971 | Fed. Rep. of Germany . |
| 2069514 | 9/1971 | France . |
| 7916168 | 1/1981 | France . |
| 2042166 | 9/1980 | United Kingdom ........... 356/336 |
| 2044445 | 10/1980 | United Kingdom . |

*Primary Examiner*—F. L. Evans
*Assistant Examiner*—Joel L. Harringa
*Attorney, Agent, or Firm*—Lerner, David, Littenberg, Krumholz & Mentlik

[57] ABSTRACT

Apparatus for identifying multiparametric properties of particles, comprising:
 a non-divergent quadric reflector,
 a transparent capillary tube passing through the focus of said reflector,
 at least one means of irradiating the focus,
 a mask obstructing the non-reflected scattered rays,
 a photosensitive cell receiving the reflected scattered rays,
 and means of processing the signals.

An application to the monitoring of latex particle size distribution is described.

12 Claims, 3 Drawing Figures

OPTICAL APPARATUS FOR IDENTIFYING THE INDIVIDUAL MULTIPARAMETRIC PROPERTIES OF PARTICLES OR BODIES IN A CONTINUOUS FLOW

The present invention relates to the measuring of certain parameters of very small particles of micron size appearing either in powdery form or in suspension in a liquid or gaseous fluid, and in particular to an optical apparatus for identifying individual multiparametric properties of particles or cells moving in a continuous flow.

There are a number of fields in which it is necessary to determine at least some of the physical characteristics of particles in order to establish whether they satisfy specific reference criteria relating to the application or use to which they will be put.

For example, it is sometimes necessary to be able to count, with considerable accuracy, the number of particles entering or leaving an environment or medium, or further, to be able to determine the particle size distribution leading to an average value for a given sample or enabling subsequent sorting of particles.

In other fields some knowledge of the shape of particles is required.

In all cases, few satisfactory techniques have been evolved in the prior art.

French patent 71-01 091 discloses certain improvements to the granulometric analysis of a powdery substance with the help of a laser. The technique therein disclosed involves aiming the laser beam at a transparent, small-diameter duct designed to be traversed by the powder to be analyzed. The laser beam, having intersected the duct, strikes a system for the analysis of scattered rays as diffracted in the course of the beam's passage through the medium to be measured.

Although this technique effectively provides a certain number of global measurements, it deserves to be emphasized that it will not satisfactorily provide individual parametric data about the particles, if so required.

Said technique may properly be qualified as global or macroscopic and does not provide an indication concerning at least one of the parameters of each particle taken individually.

The apparatus according to the present invention remedies the above-stated disadvantages and enables the identification of the multiparametric properties, such as the size, volume and absorption of deformable or solid particles for which a measurement of individual physical characteristics must be made.

The object of the invention is to provide an apparatus enabling the fast and highly accurate processing of samples of particles flowing continuously through said measuring apparatus.

An advantage of the multiparametric identification apparatus according to the invention is that it enables the collection of optical data over a volume of at least $3\pi$ steradians, centered on each particle to be identified, such as to obtain for each particle a range of data specific thereto, resulting in a finely detailed identification.

Accordingly, the apparatus according to the invention comprises:

a non-divergent quadric reflector,
a transparent capillary tube passing through the focal point of said reflector and serving as a flow-path for individual particles in suspension,
at least one means of irradiation, being aimed in a direction normal to the axis of said tube at the section of said tube passing through the above-mentioned focal point,
a mask blocking the non-reflected scattered rays from said radiating means,
a detecting means for receiving the various reflected scattered rays,
and means for processing and exploiting the signals from the detecting means.

Another advantage of the apparatus according to the invention is that it can make use, in terms of the radiating means, of any wavelength, from ultraviolet radiation to infrared radiation and including visible light.

Various other features of the invention will be made apparent on reading the following description with reference to the accompanying drawing.

BRIEF DESCRIPTION OF THE DRAWINGS

As shown in FIG. 1, the apparatus for the multiparametric identification of diverse particles, whether solid or deformable, comprises a non-divergent quadric reflector 1 mounted on any suitable support, not shown in the drawing. The term quadric reflector means any paraboloidally or ellipsoidally shaped mirror.

The reflector 1 is associated with a capillary tube 3 made of a transparent material. Capillary tube 3 is given a useful internal diameter related to the average dimension of the particles to be identified, such as to alloy only a single one of said particles to flow through at one time.

The particles move through capillary tube 3 by being carried by a suitable liquid impelled into laminar flow within the tube by a pump 4 operable to draw from a reservoir 5 containing the suspension.

Tube 3 can be made from any of several suitable materials, as will be familiar to those versed in the art, notably glass.

Tube 3 is arranged with respect to reflector 1 such that a straight section of said tube passes through reflector focus F. In the embodiment of the invention depicted in FIG. 1, tube 3 enters through the apex of the reflector 1 and extends along the axis of revolution x—x' of said reflector.

Figure 1:
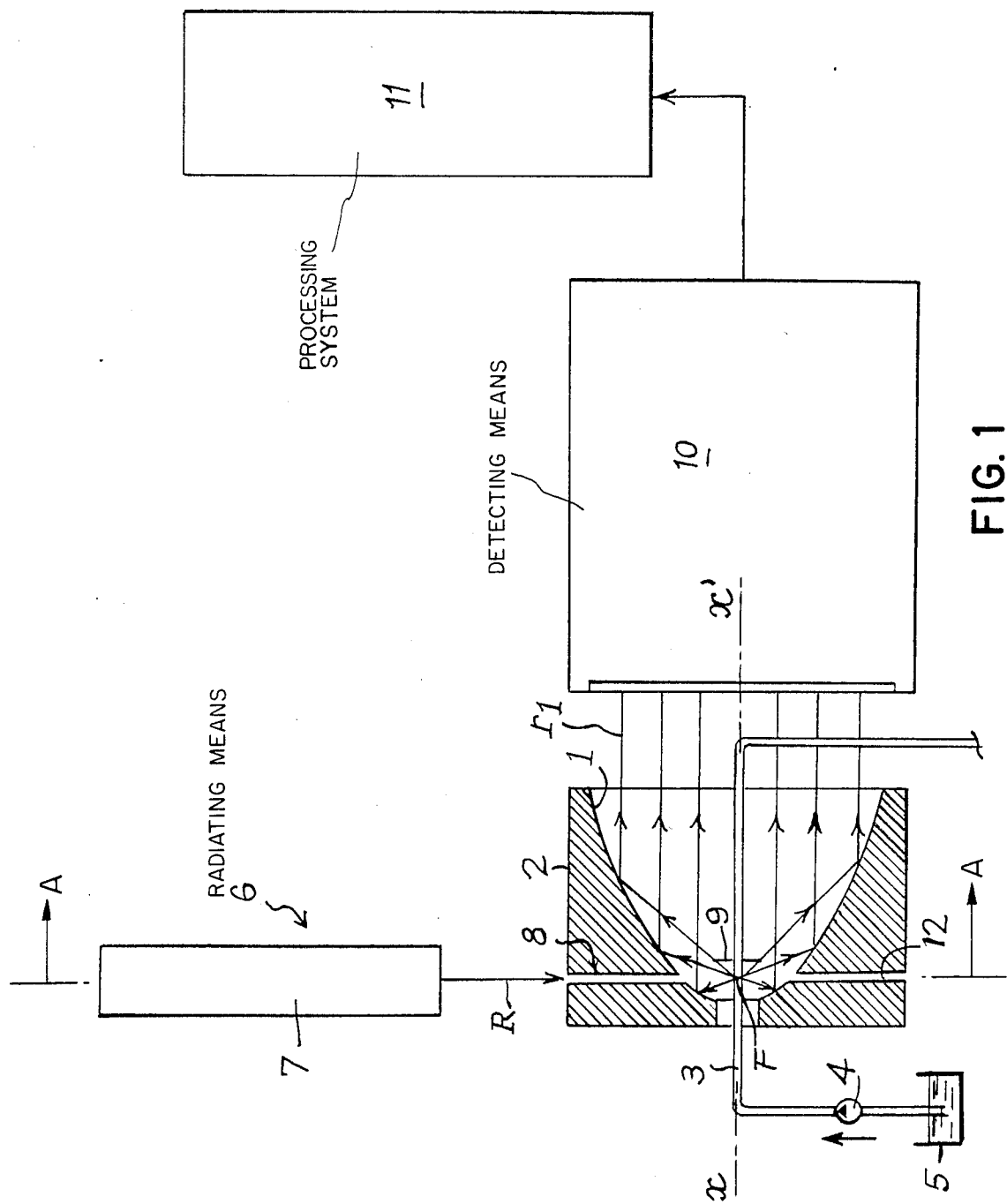
FIG. 1 is a schematic drawing of the multiparametric identification apparatus according to the invention.
Figure 3:
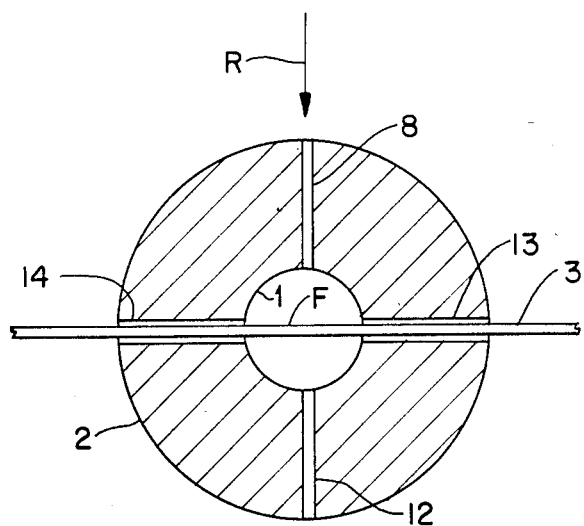
FIG. 3 is a cross-sectional view of another embodiment of the present invention taken along the lines A—A of FIG. 1.

It should be readily understood by those versed in the art however that tube 3 could, without departing from the spirit and scope of the invention, be arranged so that a straight section thereof will pass through focus F following a radial direction with respect to axis x—x', for example in a direction perpendicular to the plane of the drawing. This feature is shown in FIG. 3 wherein there is shown a cross-sectional view of reflector 1 along line A—A of FIG. 1. As in FIG. 1, reflector 1 in FIG. 3 is provided with radially formed hole 8 and port 12, which is diametrically opposite of hole 8 in the reflector. In this manner, a beam of radiation R from source 7 as shown in FIG. 1 is directed through hole 8 and focus F of reflector 1. If the beam of radiation R is not scattered at focus F, it then exits through port 12. Reflector 1 is also provided with ports 13 and 14 horizontally positioned therethrough. Capillary tube 3 is inserted through ports 13 and 14 whereby tube 3 enters reflector 1 and passes through focus F such that it is horizontally positioned in a radial direction and perpendicular to the axis of rotation x—x' (as shown in FIG. 1) of reflector 1. In this manner, the beam of radiation R will intercept tube 3 at focus F and ether scatter upon striking particles flowing through tube 3 or pass through tube 3 and exit out port 12.

Tube 3 extends beyond the opening of reflector 1, whereafter it is directed to a receptable, a device or any other means for utilizing, sorting, receiving or otherwise dealing with the particles.

The apparatus according to the invention further comprises at least one radiating means represented as a whole by item 6. Said radiating means includes a source 7 operable to emit a beam designed to be directed in a direction normal to the straight section of tube 3 passing through focus F while at the same time being aimed at said focus. Accordingly, means 6 could be arranged to strike focus F after passing through the apex of the reflector if tube 3 were to be arranged radially as suggested above.

Figure 2:
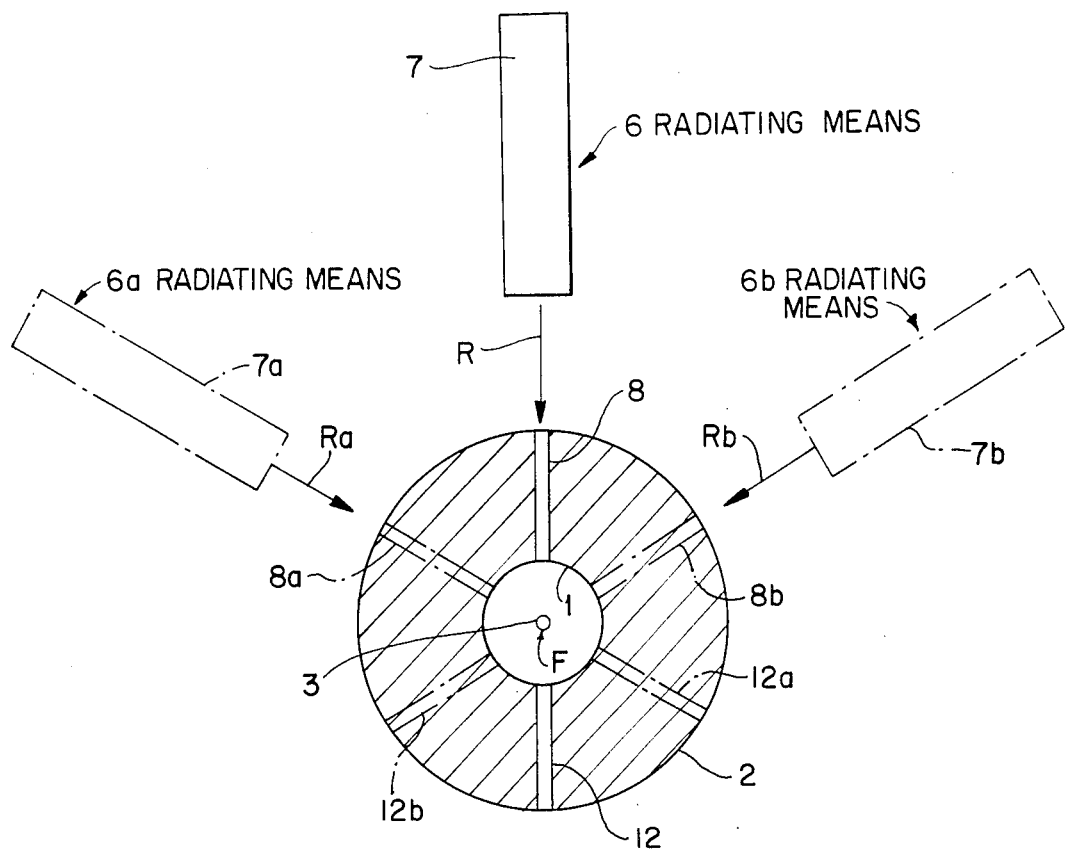
FIG. 2 is a cross-sectional view of another embodiment of the present invention taken along lines A—A of FIG. 1.

In the case where means 6 is arranged radially, as shown in FIG. 1, several sources 7 can be disposed peripherally and spaced at equal or unequal angular distances apart (see FIG. 2). Source 7 preferably consists of a laser the characteristics whereof (power and wavelength) are selected to suit the physical particularities of the particles to be identified. In all instances, the radiating means must be selected or adjusted so that the dimension of the irradiated spot at focus F is of the same order as that of the particle to be measured.

Radiating means 6 further comprises, in the case of its radial arrangement, a hole 8 radially formed in reflector 1, serving to guide the beam from source 7 toward focus F.

Referring to FIG. 2, there is shown a cross-section taken along line A—A of FIG. 1 wherein there are exhibited a plurality of radiating means 6a, 6, and 6b, respectively, rather than a single radiating means. Each of the radiating means 6a, 6, and 6b is comprised of a source of radiation 7a, 7, and 7b, respectively, which emit an individual beam of radiation Ra, R, and Rb, respectively, of different wavelengths which are then passed through holes 8a, 8, and 8b formed in reflector 1. As with the embodiment for a single radiating means 6 as shown in FIG. 1, the beams of radiation Ra, R, and Rb pass through, respectively, holes 8a, 8, and 8b in reflector 1 such that the beams of radiation Ra, R, and Rb are directed to strike tube 3 at focus F and scatter upon striking a particle in tube 3 or, if not scattered, pass through tube 3 out outlet port 12a, 12, and 12b, respectively, also formed in reflector 1.

The apparatus further comprises a mask 9 the surface area whereof is so designed as to obstruct those scattered rays not reflected by reflector 1 and to render observable only those scattered rays being reflected by reflector 1. In the embodiment depicted in FIG. 1, the mask 9 is support by the tube 3 and is given an area not exceeding the cross-sectional area of the hole provided in the apex of the reflector for the passage of tube 3. The specific location of mask 9 on tube 3 can be adjusted to match the area of the active portion of a detecting means 10 designed to receive and use the diffracted rays reflected from the reflector. Said detecting means may be either a photoelectric sensor or an optical scanner. Said detecting means 10 feeds the signals collected to a processing system 11.

For instance, detecting means 10 can actually consist of a video camera, the focus thereof being aimed along axis x'—x.

The above-described apparatus operates as follows.

The source 7 is turned on to emit a beam striking focal point A. As long as duct 3 is not being traversed by a particle and only the carrying liquid is flowing therethrough without a load, the beam, represented in the drawing by arrow R, does not become diffracted and passes through the wall of reflector 1 via a port 12 purposely formed diametrically opposite hole 8 in the reflector.

However, when a particle moving through tube 3 intersects the beam in passing through focus F, the beam is diffracted spatially and the resulting scattered rays are directed to reflector 1. Said scattered rays are reflected parallel to one another and directed toward the detecting means 10, thereby transforming the as-emitted three-dimensional data into a collection of two-dimensional data.

The luminous data received by detecting means 10 are processed, either directly or by the intervention of processing system 11, so as to provide a logical or analogical rendering of particle identification parameters.

Said parameters may be of a variety of orders, given the constructional specification of the apparatus according to the invention.

In fact, each irradiation of a particle at focus F of reflector 1 provides an indicatrix of diffraction over a range of at least $3\pi$ steradians and consequently enables a great number of specific data items, as supplied by the diffracted rays and corresponding to specific physical characteristics of the particle, to be taken into consideration.

It is thus possible to identify the size of a particle as required for continuous-flow granulometry. Since the data collected come from a spatial envelope covering at least $3\pi$ steradians, it is also possible to assess shape factors for each particle and thus to effect a selection and/or a counting operation, as required, within a population or a sample made up of different types of particles, using conventional mathematical and computerized signal identification and processing techniques. The invention further enables a mere counting of particles if such is required, for example to determine the quantity of given particles present in a given fluid medium.

The apparatus can moveover be used to record multiple parameters derived from optical properties, including the properties seen after staining the particles or bodies under study with fluorochrome.

All of these individual indentifications can be carried out on a continuous flow or stream of particles with great sensitivity since the data are collected from a nearly full spatial envelope.

By combining the processing means for the received data, it is possible to carry out, simultaneously, a plurality of parametric identifications of particles in any given gas or liquid. It is thus possible to make a global count or a differential count of particles according to shape and, for example, to establish the relative proportion of each type of particle within a given medium, ie. their concentration per unit of volume.

One of the advantages of the apparatus according to the invention resides in the simplicity of the equipment involved and its low cost in terms of both manufacturing and maintenance. Reflector 1 for example is a commercial item requiring only minor modification for use in the apparatus, involving the creation of one or more openings required for accommodation of capillary tube 3 and of the beam path for the beam of source 7.

Another advantage is the fast processing capability of the apparatus which enables multiparametric identification on a continuous flow basis and online or offline, batch processing pursuant to storage of the data pertaining to each detected particle.

It should be emphasized that the apparatus according to the invention can be used for multiparametric identification of both solid and liquid particles, suspended in a fluid carrying them through the tube 3.

Such an apparatus can thus enable shape factors of such particles, where applicable, to be appreciated, based on any surface treatment additives which may be applied to them directly or through the carrying medium, as well as other factors such as their frequency of occurence and their number.

In an example of application to the monitoring of the particle size distribution of 10μ-diameter latex particles, the apparatus is specified as follows:

| Capillary tube 3 | internal diameter on the order of 25 to 30μ |
|---|---|
| Flow rate | a few milliliters per sec. |
| Carrying fluid | transparent, non-diffusing and having a different refractive index from the particles |
| Suspension concentration per volume | roughly 1% |
| Laser power output | a few milliwatts |
| Laser wavelength | 632.8 nm |
| Reflector 1 | paraboloidal |
| detecting means 10 | video camera with silicon target |

As previously stated, the apparatus can use n radiating means, in which case said means will emit beams with different wavelengths and will be arranged to converge at focus F. The processing system in such a case is provided with color filters enabling the various reflected diffracted rays to be sorted.

The invention should not be construed as being limited to the embodiment described and illustrated, as various modifications can be made to it without departing from the spirit and scope of the invention.

What we claim is:

1. An optical apparatus for identifying individual multiparametric properties of particles or bodies moving in a continuous flow, said apparatus comprising:
   an open-ended, non divergent quadric reflector having a focal point,
   a transparent, continuous capillary tube passing through said focal point of said reflector and providing for the movement, individually, of particles in suspension in a fluid medium,
   radiating means capable of directing a beam of radiation normal to the direction of particle movement in said capillary tube through said focal point, said beam of radiation upon striking said particle producing different rays,
   a mask obstructing a portion of said diffracted rays scattered by a particle intersecting the incident beam of the radiating means at the reflector focus and not striking the reflector,
   a detecting means for receiving the various reflected scattered rays for producing a signal thereof,
   and means for processing and using said signals supplied by said detecting means.

2. An apparatus as in claim 1, wherein said capillary tube passes through the apex of said reflector and extends along the axis of revolution of said reflector and wherein at least one radiating means is provided, comprising a source positioned in radial relation to the reflector and emitting a beam aimed at said reflector focus.

3. An apparatus as in claim 2, wherein said mask is supported by said tube.

4. An apparatus as in claim 1, wherein said capillary tube is installed in a plane perpendicular to the reflector's axis of revolution, said capillary tube passing through said focus where it intersects the beam of at least one radiating means.

5. An apparatus as in claim 2, comprising a plurality of radiating means each emitting at a different wavelength.

6. An apparatus as in claim 5, wherein a borehole is provided through the reflector for each radiating means at a point diametrically opposite the point occupied by said means.

7. An apparatus as in claim 1, wherein the radiating means provides an irradiated spot at the focus on the same order of size as the particle to be identified.

8. An apparatus as in claim 1, wherein the radiating means comprises a laser beam source.

9. An apparatus as in claim 1, wherein the detecting means consists of a photosensitive sensor.

10. An apparatus as in claim 1, wherein the transparent capillary tube has a useful internal cross-section substantially related to the average dimension of the particles under study so as to allow only a particle by particle progress through the measuring space intersected by the radiating means.

11. An apparatus as in claim 1, wherein the detecting means consists of an optical scanner.

12. An apparatus as in claim 1, wherein the detecting means consists of a video camera.

* * * * *

UNITED STATES PATENT AND TRADEMARK OFFICE
CERTIFICATE OF CORRECTION

PATENT NO. : 4,606,636

DATED : August 19, 1986

INVENTOR(S) : Monin et al.

It is certified that error appears in the above-identified patent and that said Letters Patent is hereby corrected as shown below:

```
Column 2, line 37, "alloy" should read --allow--.
Column 3, line 7, "ether" should read --either--.
Column 4, line 8, "A" should read --F--.
Column 4, line 50, "moveover" should read --moreover--.
Column 6, line 7, "different" should read --diffracted--.
```

Signed and Sealed this

Twenty-third Day of December, 1986

*Attest:*

DONALD J. QUIGG

*Attesting Officer*  *Commissioner of Patents and Trademarks*